United States Patent [19]
Jensen

[11] Patent Number: 5,591,447
[45] Date of Patent: Jan. 7, 1997

[54] WOUND DRESSING HAVING A CONTOURED ADHESIVE LAYER

[75] Inventor: Ole R. Jensen, River Vale, N.J.

[73] Assignee: Hollister Incorporated, Libertyville, Ill.

[21] Appl. No.: 514,905

[22] Filed: Aug. 14, 1995

Related U.S. Application Data

[63] Continuation of Ser. No. 760,167, Sep. 16, 1991, abandoned, which is a continuation-in-part of Ser. No. 590,684, Oct. 1, 1990, abandoned.

[51] Int. Cl.$^6$ ..................................... A61F 13/00
[52] U.S. Cl. ........................ 424/443; 424/445; 424/446; 424/447; 424/448; 604/332; 604/333; 604/341
[58] Field of Search ..................... 424/443, 445, 424/446, 447, 448; 604/332, 333, 341

[56] References Cited

U.S. PATENT DOCUMENTS

| | | | |
|---|---|---|---|
| 3,339,546 | 9/1967 | Chen | 128/156 |
| 4,725,272 | 2/1988 | Gale | 424/448 |
| 4,830,856 | 5/1989 | Peppers | 424/449 |
| 4,867,748 | 9/1989 | Samuelsen | 604/336 |

*Primary Examiner*—D. Gabrielle Phelan
*Attorney, Agent, or Firm*—Tilton Fallon Lungmus

[57] ABSTRACT

An improved wound dressing having an adhesive layer (26, 426) containing one or more hydrocolloids dispersed in a viscous elastomer, a flexible water-impervious backing layer (22, 322, 422) on one side of the adhesive layer, and a removable release layer (28, 328, 428) on the adhesive layer's opposite side. The dressing includes a body portion (36) with a stair-like outer contour merging with a peripheral flange (38, 238, 338, 438) of reduced thickness. The flange (38, 238, 338, 438) is required to have a width of at least 5 mm. and the thickness of the adhesive layer of that flange is no greater than 0.5 mm., for purposes of overcoming prior problems of adhesive flow, fluid channeling, leakage, and unintentional detachment.

11 Claims, 3 Drawing Sheets

WOUND DRESSING HAVING A CONTOURED ADHESIVE LAYER

RELATED APPLICATION

This application is a continuation of application 07/760,167, filed Sep. 16, 1991, now abandoned, which in turn was a continuation-in-part of application Ser. No. 07/590,684, filed Oct. 1, 1990, now abandoned.

TECHNICAL FIELD

The present invention is believed to be found in the field of dressings or bandages for attachment to the body by means of skin-friendly and fluid absorbent adhesive. The bandage of the present invention is selectively contoured to control the flow of adhesive or fluid from the wound area and to prevent the entry of contaminants into the wound.

BACKGROUND ART

Dressings or bandages utilizing a water-absorbent adhesive are well known in the industry. One example of the prior art is U.S. Pat. No. 3,339,546 as issued to Chen on Sep. 5, 1967.

The shaping of an adhesive layer is the subject of U.S. Pat. No. 4,867,748 issued to Samuelsen on Sep. 19, 1989. The Samuelsen patent attempts to solve the problem of adhesive flow by beveling the peripheral edge of the dressing to ¼ (one-quarter) of the thickness of the pad portion of the dressing.

The above-cited prior art does not fully address the problem of applying a dressing or bandage to a contoured or curved portion of a patient's body and subsequently keeping the dressing in place. One disadvantage of placing the prior art dressings on the contoured portions of a patient's body is a wrinkling of the dressing due to the thickness of the adhesive layer and the movement of the user's skin. This wrinkling effect creates a channel-like passageway in the peripheral surface of the dressing. This channel-like passageway will allow contaminants into the wound or may allow fluids from the wound and/or adhesive to exit the border of the dressing.

In view of all of the patented and otherwise known wound dressings or bandages, there exists a need for a disposable dressing which is economical to manufacture, controls the flow of the dressing adhesive while virtually eliminating the wrinkling effect of and at the dressing's sealing surface. There is also a need to provide a dressing which will remain in place on the body for extended periods. The desired bandage should also resist the effects of bathing or showering which may induce the undesirable and premature removal of the dressing.

DISCLOSURE OF INVENTION

This invention may be summarized, at least in part, with respect to its objects. It is an object of this invention to provide and it does provide a dressing or bandage which has a selectively contoured edge portion which effectively restricts the flow of adhesive from the dressing.

It is an other object of this invention to provide and it does provide an improved dressing or bandage which has a contoured peripheral edge which easily flexes to resist a wrinkling effect or channeling.

One aspect of this invention lies in the discovery that in a dressing having an adhesive layer, in which the adhesive consists essentially of a blend of water soluble or swellable hydrocolloids and a water-insoluble viscous gum-like elastic binder, and a flexible and preferably stretchable water-impervious backing layer covering a surface of the adhesive layer, problems of adhesive flow, channeling, and leakage of wound exudate and other fluids around the edges of the dressing may be eliminated or at least greatly reduced if the dressing is reduced along its periphery to provide a flange that has a width (measured in a direction from the body of the dressing to the edge of the flange) of at least 5 mm., preferably at least 10 mm., and in which the thickness of the adhesive layer does not exceed 0.5 mm. and is preferably less than 0.3 mm. A flange meeting such requirements serves as a highly effective transition between the stretch and flex characteristics of the body of the dressing and those of the patient's skin to which the adhesive layer is adhered, resulting in a dressing having the absorbent, wound-protecting advantages of prior dressings without the disadvantages of chaneling, leakage, and adhesive flow found in such earlier dressings.

In addition the above summary, the following disclosure is detailed to insure adequacy and aid in the understanding of this invention. This disclosure, however, is not intended to cover each new and inventive concept, no matter how it may later be disguised either by variations in form, or additions by further improvements. For this reasons, there has been chosen specific embodiments of a wound dressing or bandage. These specific embodiments have been chosen for the purpose of illustration and description, as shown in the accompanying drawings.

BRIEF DESCRIPTION OF DRAWINGS

FIG. 9 represents a wound dressing of the present invention, in reduced scale, with a central aperture. This embodiment is particularly useful with ostomy bags and the like.

FIG. 10 represents a further embodiment of the dressing, in reduced scale, when used with an ostomy bag and the like.

The drawings disclose certain details of construction associated with improved wound dressings or bandages embodying this invention. Such details are for the purpose of explanation, but the structural details may be modified without departure from the concept and principles of the invention. It is to be noted that the various figures of the drawings have been exaggerated with respect to the relative thickness of the various components which are shown and described. It is believed that showing these components in exaggerated form will aid in the understanding of the invention. It is anticipated that this invention may be incorporated into embodiments other than as shown.

MODES FOR CARRYING OUT THE INVENTION

Figure 2:
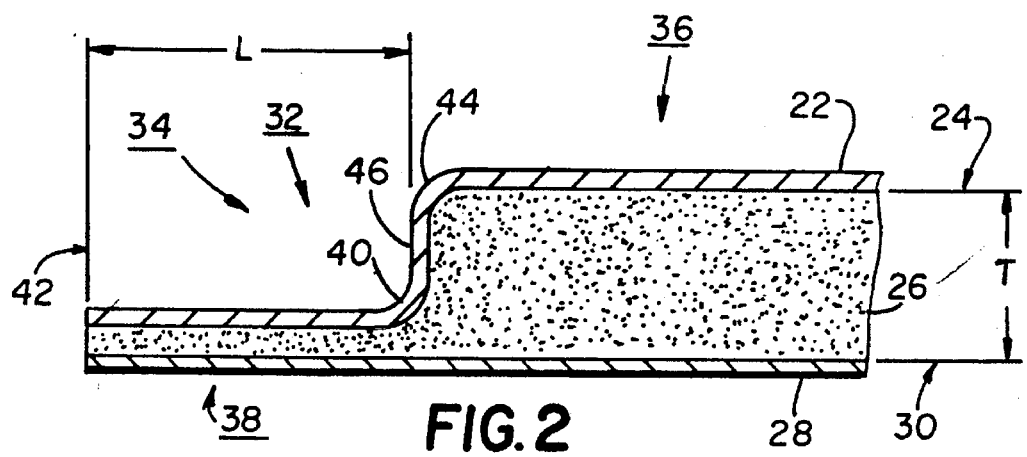
FIG. 2 represents fragmentary sectional view, in an enlarged scale of one embodiment of the present invention. This view particularly shows the curved corner portions of the wound dressing.
Figure 1:
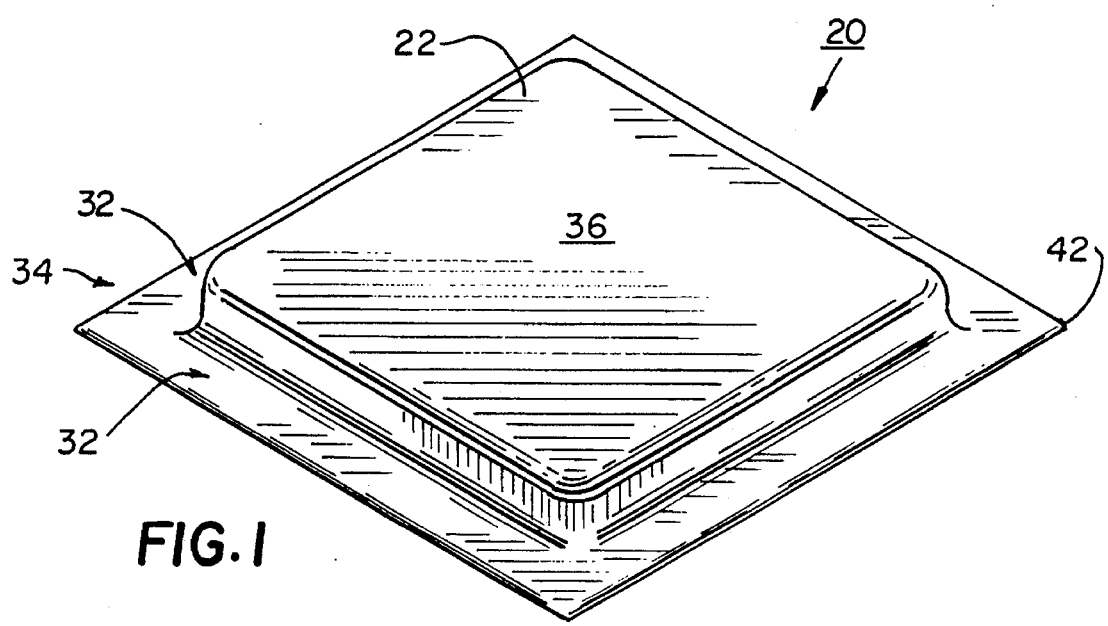
FIG. 1 represents a perspective view of an improved wound dressing or bandage of the present invention.

Referring in particular to FIG. 1, there is shown a contoured dressing or bandage, generally identified at 20, for covering a wound. The dressing 20 has a water-impervious backing layer 22 which is fully connected to top surface 24 of an adhesive layer 26. This adhesive layer 26, which may be more clearly seen in FIG. 2, is of the fluid absorbing type that swells as it absorbs moisture and has both wet and dry tack. Such an adhesive material is well-known and generally consists of a hydrocolloid, or a mixture of hydrocolloids, dispersed in a viscous, water-insoluble, elastomeric binder. Such an adhesive material consists essentially of from about 50 to 70% by weight of a water soluble or swellable hydrocolloid, or a mixture of such hydrocolloids, selected from the group consisting of sodium carboxymethylcellulose, calcium carboxymethylcellulose, pectin, gelatin, high molecular weight carbowax, carboxypolymethylene, and polyvinyl alcohol, dispersed in a viscous elastomer selected from the group consisting of polyisobutylene, natural rubber, silicone rubber, acrylonitrile rubber, and polyurethane rubber. As disclosed in the aforementioned U.S. Pat. No. 3,339,546, a particularly effective adhesive composition is believed to be composed of polyisobutylene in which is dispersed a mixture of sodium carboxymethylcellulose, pectin, and gelatin.

A protective and removable release layer 28, such as a silicone release paper, completely covers the substantially flat bottom surface 30 of adhesive layer 26.

Still referring to FIG. 2, it may be seen that the top surface 24 of the adhesive layer is contoured along its periphery 32 in a more or less stair-like profile 34. This contouring of the adhesive layer 26 results in a thick absorbent body portion 36 and a relatively thin peripheral flange 38 extending outwardly from the body portion for a predetermined width or length L. It has been found that dimension L and the thickness of the adhesive layer of the flange are of particular importance in providing a dressing that avoids channeling and leaking in use. The thickness T of the adhesive layer of the body portion substantially exceeds 0.5 mm. and preferably falls within the range of about 0.75 to 3.0 mm. Because of such thickness, the adhesive layer of the body portion tends to control the physical characteristics of the dressing and limit its conformability with the wound site and surrounding skin areas and its capability of adapting to anatomical changes as the patient moves or is moved. As a skin surface bends, flexes, and contracts beneath such body portion, channels are found to develop because of the inability of the thick adhesive layer to comply with or conform to such changes. If flange 38 were omitted, such channels would extend to the edge of the dressing and the edge might even break away or release from the skin because of the sharp differences in behavior between the skin and the dressing along that edge. Flange 38 therefore serves as a flexible transition from the relatively thick body portion 36 to the skin area immediately surrounding the dressing. However, to avoid channeling and leakage that might result, it is essential that the adhesive layer of the flange not only be relatively thin but that it have at least a minimum width L.

The thickness of the adhesive material of the flange should not exceed 0.5 mm., and should preferably fall within the range of 0.1 to 0.3 mm., to achieve effective conformability to the skin and its changable contours and to avoid flow or extrusion of the adhesive beyond the periphery of the dressing when it is worn. The minimum width of the flange depends in part on the characteristics of the material selected for backing layer 22. If, for example, the backing layer is highly stretchable, then the flange may have a width as narrow as 5 mm. A width of 5 mm. is believe to be a minimum dimension L for avoiding the formation of wrinkles or channels that extend to the edge of the dressing, and thereby cause detachment and leakage, even with a highly compliant backing layer. If the backing layer is flexible but substantially non-stretchable, then a minimum flange width of 10 mm. or more may be necessary. Therefore, in general, the peripheral flange 38 should have a minimum width falling within the range of 5 to 15 mm.

In the embodiment illustrated in FIG. 2, flange 38 has a substantially uniform thickness from the lower interior corner 40 to a selected point at or near the extreme edge 42 of the dressing. The upper exterior corner 44 and the lower interior corner 40 are selectively curved. The radii selected and resulting at each of these corners is dependent on the forming characteristics of the backing layer 22. It is to be noted that when the sum of the radii used at the upper exterior corner 44 and the lower interior corner 40 are less than the thickness T of the body portion 36, a substantially vertical line segment 46 tangentially connects the radii of corners 40 and 44. It is to be understood, however, that line segment 46 may lie at angles other than vertical with respect to the substantially flat bottom surface, such as between 5 degrees to 89 degrees.

Figure 3:
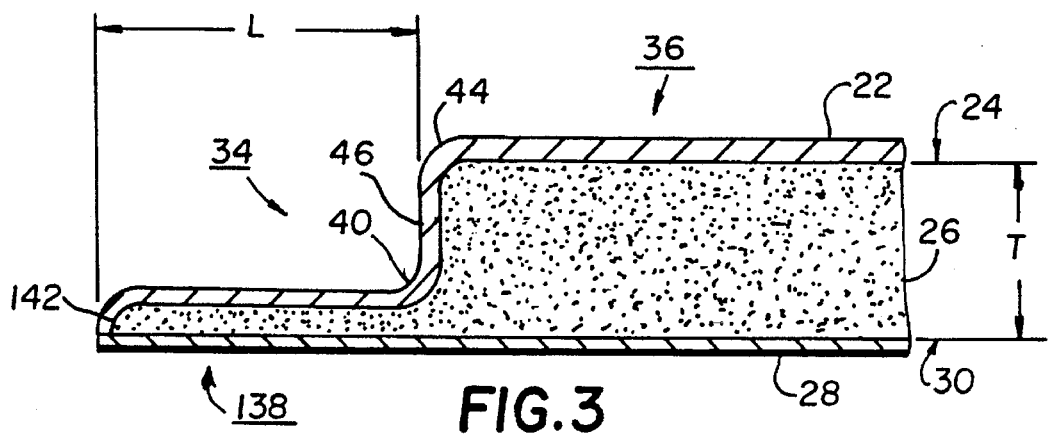
FIG. 3 represents a fragmentary sectional view, in an enlarged scale, of a first alternate embodiment of the present invention. This view particularly shows the contour of the edge portion of the wound dressing's peripheral flange.

Referring to FIG. 3, the first alternate embodiment is substantially the same as the embodiment shown in FIGS. 1 and 2. Water-impervious backing layer 22 and adhesive flange 138 have an additional curved portion formed at the extreme edge 142. The preferred radius is equivalent to the thickness of the thin flange 138. In this embodiment, the water-impervious backing layer 22 is carried around the edge 142 to be substantially coincident with the bottom surface 30. Such an arrangement provides a substantially complete covering of the adhesive layer 26 by the backing layer 22 when the dressing is adhered to the skin.

Figure 4:
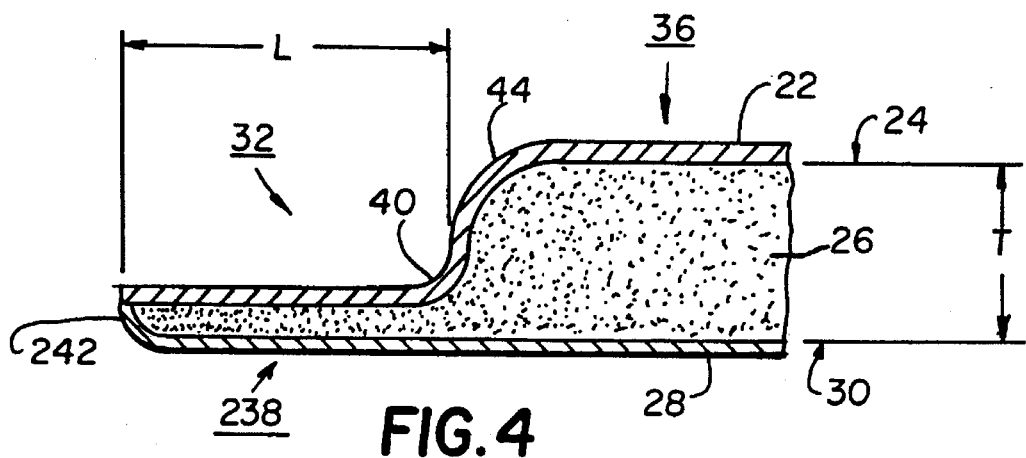
FIG. 4 represents a fragmentary sectional view, in enlarged scale, of a second alternate embodiment of the present invention. This view particularly shows the contoured peripheral portion as two radiused corners which are tangentially connected to form a continuously curved profile. Also shown is the form of the protective release layer.

Referring to FIG. 4, a second alternate embodiment of a dressing is shown. This embodiment is very similar to the embodiment shown and described in connection with FIGS. 1 and 2. Upper exterior corner 45 and lower interior corner 40 are formed by a substantially S-shaped curve. The sum of the radii is equal to the thickness of the body portion 38 less that of the thin flange portion 238. This embodiment shows the protective release layer 28 being formed at the extreme edge 242. Such extreme edge 242 may have the release layer radiused within a range of one to four times the thickness of the flange portion 238. This arrangement will also provide for the substantially complete enclosure of the adhesive layer 26 when adhered to the skin. The radiused edge 242 of the adhesive layer 26 will allow the backing layer 22 to be pressed against the skin of the patient by manipulation.

Figure 5:
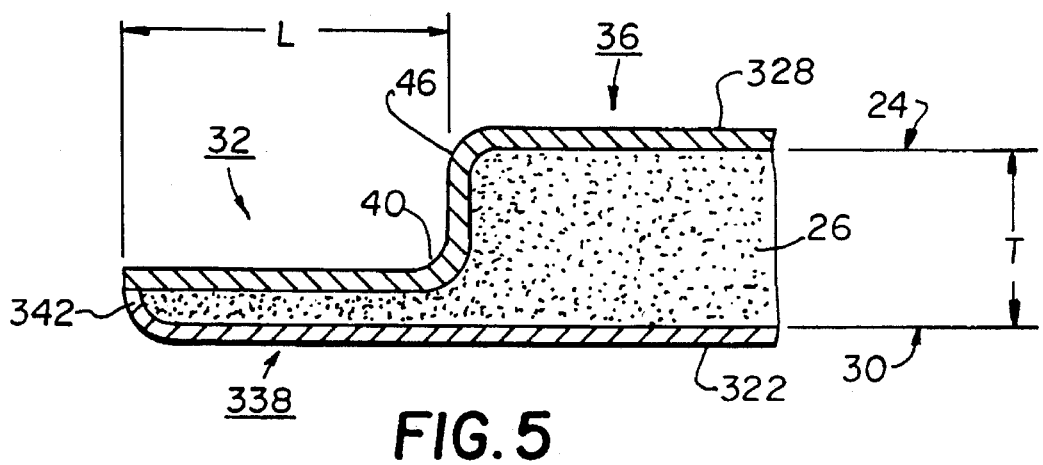
FIG. 5 represents a fragmentary sectional view, in an enlarged scale, of a third alternative embodiment of the present invention, this view particularly showing the lamination of a water impermeable backing layer to the underside of the dressing.

Referring to FIG. 5, a third alternate construction of the dressing of the present invention is shown and disclosed. Hydrocolloid adhesive layer 26 is contoured as in FIG. 4. A water-impervious backing layer 322 is fully connected to the substantially flat bottom surface 30 of the adhesive layer 26. A protective release layer or sheet 328 is removably attached to the top surface 24 of the adhesive layer which has been contoured with a stair-like profile 34. The extreme edge 342 of the thin flange 338 is radiused substantially as shown and described in FIG. 4.

Figure 6:
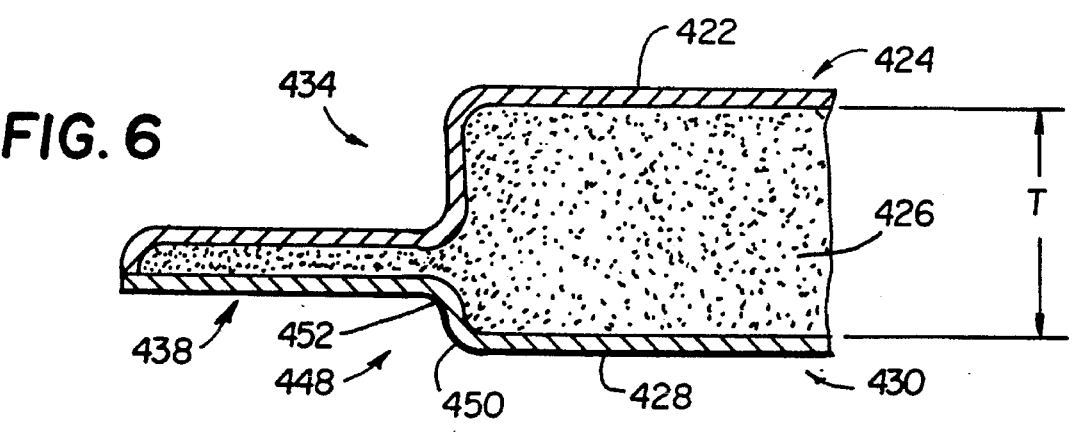
FIG. 6 represents a fragmentary sectional view, in an enlarged scale, of a fourth alternate embodiment of the present invention, this view particularly showing a double contouring of the adhesive layer.

Referring now to FIG. 6, a fourth alternate construction for a wound dressing is shown in which adhesive layer 426 is shaped on both of its major surfaces. The top surface 424 is contoured with a stair-like profile 434 similar to profile 34. The bottom surface 430 has also been profiled with a second stair-like profile 448. The bottom surface 430 has a bottom exterior corner 450 and a bottom interior corner 452. It is to be noted that the profiling of the top surface 424 and the bottom surface 430 may be similar or dissimilar with regard to size and shape and are matters of design selection. The profiling may also be symmetrical and asymmetrical with regard to the depth of the stair-like profiles 434 or 448 depending on the desired location of the thin flange 438. It is to be noted that flange 438 may have any of the configurations discussed in connection with the previous embodiments.

Figure 7:
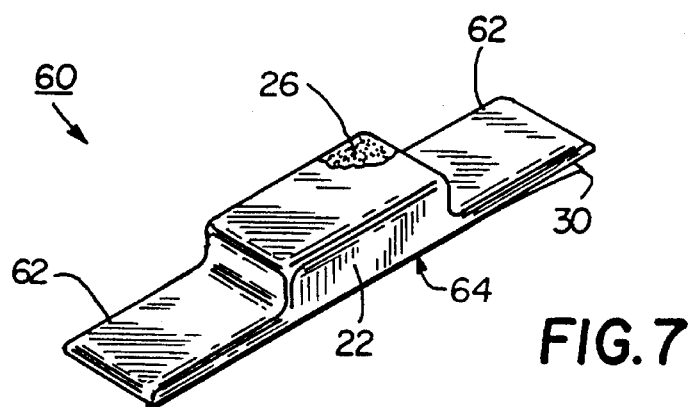
FIG. 7 represents a perspective view of a fifth alternate embodiment of the present invention, this view particularly showing a strip bandage with all edges enclosed.

In the embodiments so far described and shown, the adhesive layers are contoured on all exterior edges. Referring to FIG. 7, a fifth alternate construction is depicted wherein the dressing of the present invention is made in a more or less strip form generally identified by the numeral 60. In this embodiment, each end portion 62 is contoured using one of the stair-like profiles as described above with respect to FIGS. 2, 3, or 4. The elongated sides 64 have the backing layer 22 contoured to cover the sides of the adhesive layer 26. It may be seen that this arrangement provides for the substantially complete covering of the adhesive layer 26 by the backing layer 22. It is to be noted that a removable protective release layer 30, shown partially peeled away from the adhesive layer 26, is provided on the bottom surface of bandage 60. This embodiment may be readily substituted for conventional gauze-type strip bandages. It should also be noted that the elongated sides 64 may be contoured with thin flanges extending therefrom while the ends without thin flanges may be covered by and with the backing layer 22.

Figure 8:
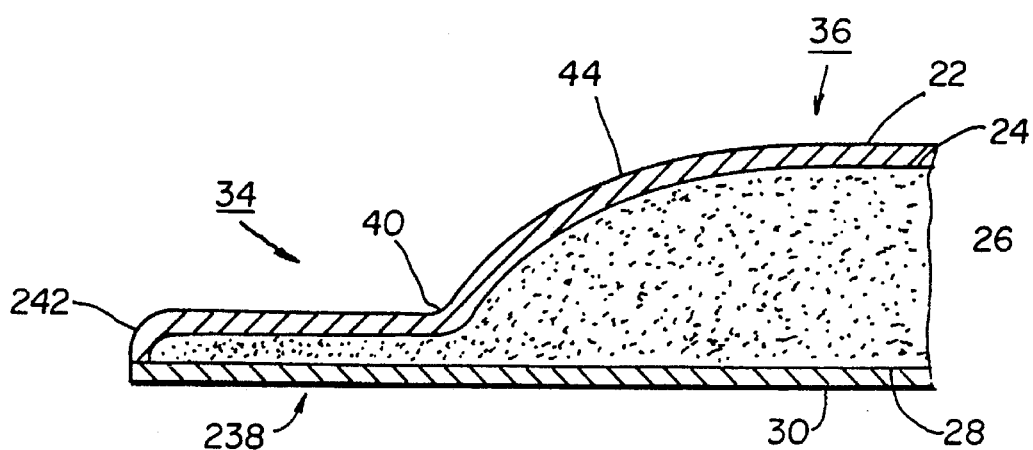
FIG. 8 represents a fragmentary sectional view, in an enlarged scale, of a sixth alternate embodiment of the present invention, this view particularly showing a large curve leading to the flange of the dressing.

Referring now to FIG. 8, it may be seen that the alternate embodiment of FIG. 4 has been further modified. In this arrangement, a curved portion, formed by at least one radius larger than the thickness of adhesive layer 26, is formed at the upper exterior corner 44. The radius at the lower interior corner 40 and the larger curved portion meet at a tangent point or cusp which, as shown, is near the lower interior corner 40. It is to be noted that this cusp point may be located at any convenient location intermediate the upper exterior corner 44 and the lower interior corner 40. It is also to be noted that the cusp point may be at an intersection of each curved contour of the upper exterior corner 44 and the lower interior corner 40 absent a tangential arrangement.

In all of the embodiments described, the composition of the adhesive layers are the same as layer 26 of the first embodiment of FIGS. 1, 2, as are the widths of flanges 38, 138, 238, 338, 438, the thicknesses of the adhesive layers of those flanges, and the thicknesses T of body portions 26, 426. The backing layers 22, 322, 422 of all embodiments are thin, highly flexible or deformable, and water-impervious. In general, their thickness should fall within the range of 0.05 to 0.20 mm. to achieve the forming and flexing characteristics desired. A polyethylene film may be used, and particularly effective results may be achieved with stretchable, elastomeric films formed of polyurethane which has the further advantage of gas (including water vapor) transmissibility. It is to be understood, however, that other flexible, water insoluble polymeric films known in the art may be used. Furthermore, the backing layers may be formed from closed-cell polymeric foam particularly one with an integral skin covering the side facing away from the adhesive layers. Foam layers formed of polyurethane or polyethylene are suitable, but other polymeric foams having similar properties may be used.

It can also be seen that the stair-like profile of the present invention will be economical with respect to the use of adhesive material in the thin flanges of the various embodiments. Such a saving of material becomes evident when a dressing of the present invention is compared with an equal sized prior art dressing having a beveled periphery.

Figure 9:
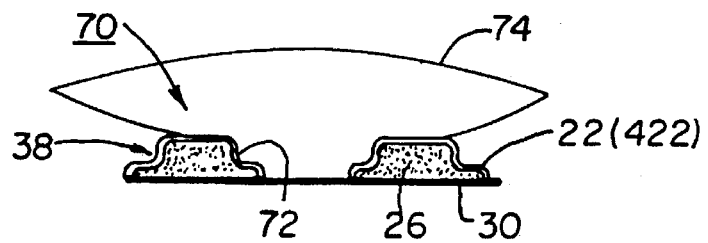

Referring to FIG. 9, the present invention may take the form of an annular member 70 having a thin outer flange 38 and a thin inner flange 72. The backing layer 22 (422) is welded to an ostomy bag 74. A protective and removable release layer 30 is provided on the side of the adhesive layer opposite from backing layer 22. In this embodiment, the backing layer completely covers one side of the adhesive layer 26 and its thin inner and outer flanges, as well as the edges of those flanges, thereby substantially eliminating contact of the adhesive layer from contact with body fluids when the annular member is worn.

Figure 10:
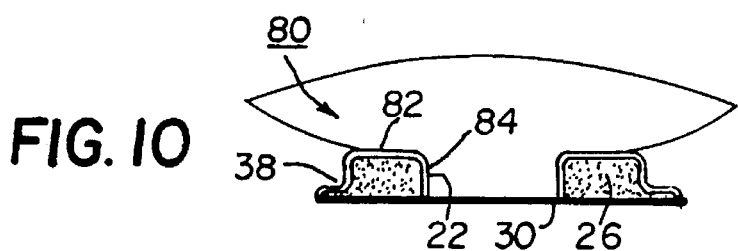

Referring to FIG. 10, annular dressing or seal 80 includes an annular adhesive layer 26 and a backing layer 22 that is attached to an ostomy bag along an annular zone 82. This annular dressing has a thin outer flange 38 and a through aperture 84, the latter being lined with backing layer 22. A detachable protective release layer 30 is provided on the side of the adhesive layer 26 opposite from backing layer 22.

In all of the embodiments, the protective and removable release layers may be opaque or transparent. A transparent release layer, such as one formed of a flexible transparent polymeric film, is particularly useful in the embodiments of FIGS. 9 and 10 because it may aid in the patient's selection of an ostomy bag assembly. To faciliate removal, the release layers may be coated with silicone or other suitable release agent along the surfaces of such layers facing the adhesive layers of dressings embodying this invention.

The curved contoured portions 40, 44, 450, and 452 have been found to be advantageous as opposed to sharp corners for providing and maintaining full contact of the backing layers and/or the release layers with the adjacent adhesive layers. This full contact is most important during storage of the dressing, since air pockets may otherwise form and air penetration of some adhesive formulations may result in dry spots on the surfaces of the adhesive layers resulting in poor adhesion and possible leakage when the dressings are used. Dry spots between the backing layers and the adhesive layers may also result in the adhesive layers having greater affinity for the skin, resulting in patches of access adhesive remaining on the skin as and when the dressings are removed.

Terms such as "left", "right", "up", "down", "bottom", "top", "front", "back", "in", "out", "interior", "exterior" and the like are applicable to the embodiments shown and described in conjunction with the drawings. These terms are merely for the purpose of description and do not necessarily apply to the position in which the wound dressing of the present invention may be used or manufactured.

While these particular embodiments of an improved wound dressing or bandage have been shown and described, it is to be understood that the invention is not limited thereto and protection is sought to the broadest extent the prior art allows.

What is claimed is:

1. An improved wound dressing comprising an adhesive layer which in use contacts a wound and surrounding normal skin; and a thin, flexible, polymeric backing layer covering one side of said adhesive layer; said adhesive layer consisting essentially of from about 50 to 70% by weight of a water soluble or swellable hydrocolloid, or a mixture of such hydrocolloids, selected from the calcium carboxymethylcellulose, pectin, gelatin, high molecular weight carbowax, carboxypolymethylene, and polyvinyl alcohol, with said hydrocolloid or mixtures of hydrocolloids being dispersed in from about 30 to 50% by weight of a water-insoluble, viscous elastomer selected from the group consisting of polyisobutylene, natural rubber, silicone rubber, arcylonitrile rubber, and polyurethane rubber; said dressing including a body portion in which the thickness of adhesive layer exceeds 0.5 mm.; and a protective release layer removably attached to and covering the side of said adhesive layer opposite from said backing layer; wherein the improvement comprises said dressing including a wide peripheral flange of reduced thickness extending outwardly beyond said body portion a distance of at least 10 mm and in which the thickness of said adhesive layer of said flange does not exceed about 0.5 mm, said flange being of substantially uniform thickness throughout its full extent.

2. The dressing of claim 1 in which said thickness of said adhesive layer of said flange falls within the range of about 0.1 to 0.3 mm.

3. The dressing of claim 1 in which said backing layer is an elastomeric and gas permeable polymeric film.

4. The dressing of claim 1 in which said flexible backing layer comprises a polymeric closed-cell foam.

5. The dressing of claim 1 in which said flange terminates in an extreme edge portion; said adhesive layer of said flange having an edge at said extreme edge portion covered by said backing layer.

6. The dressing of claim 5 in which said extreme edge portion is contoured with a radius at least equal to the thickness of said flange.

7. The dressing of claim 1 in which said body portion of said dressing has a stair profile adjacent to said outwardly extending peripheral flange; said stair profile including an exterior corner having a first curved contour and an interior corner having a second curved contour; each of said first curved contour and said second curved contour being defined by at least one radius.

8. The dressing of claim 7 in which said first curved contour of said exterior corner is tangentially connected to said second curved contour of said interior corner by and with a substantially straight line segment.

9. The dressing of claim 8 in which said line segment extends at an angle between 5 degrees and 90 degrees with respect to said flange.

10. The dressing of claim 7 in which said stair profile is along the side of said dressing provided with said backing layer.

11. The dressing of claim 7 in which said stair profile is along the side of said dressing provided with said protective release layer.

* * * * *

UNITED STATES PATENT AND TRADEMARK OFFICE
CERTIFICATE OF CORRECTION

PATENT NO. : 5,591,447
DATED : January 7, 1997
INVENTOR(S) : Ole R. Jensen

It is certified that error appears in the above-indentified patent and that said Letters Patent is hereby corrected as shown below:

Col. 7, line 20, after "the" insert -- group consisting of sodium carboxymethylcellulose, --

Signed and Sealed this

Seventh Day of April, 1998

Attest:

BRUCE LEHMAN

Attesting Officer    Commissioner of Patents and Trademarks